United States Patent [19]

Löher et al.

[11] Patent Number: 5,314,863
[45] Date of Patent: May 24, 1994

[54] ISOXAZOLINES, THEIR PREPARATION, AND THEIR USE AS PLANT-PROTECTING AGENTS

[75] Inventors: Heinz J. Löher, Hofheim am Taunus; Wilfried Schwab, Wiesbaden; Klaus Bauer, Hanau; Hermann Bieringer, Eppstein/Taunus, all of Fed. Rep. of Germany

[73] Assignee: Hoechst Aktiengesellschaft, Frankfurt am Main, Fed. Rep. of Germany

[21] Appl. No.: 856,204

[22] PCT Filed: Nov. 17, 1990

[86] PCT No.: PCT/EP90/01966

§ 371 Date: Jun. 25, 1992

§ 102(e) Date: Jun. 25, 1992

[87] PCT Pub. No.: WO91/08202

PCT Pub. Date: Jun. 13, 1991

[30] Foreign Application Priority Data

Nov. 25, 1989 [DE] Fed. Rep. of Germany ....... 3939010

[51] Int. Cl.$^5$ ................ A01N 43/40; A01N 43/80; C07D 413/06; C07D 263/08
[52] U.S. Cl. ................... 504/100; 504/191; 504/193; 504/225; 504/252; 504/271; 544/137; 546/283; 548/110; 548/237; 548/240
[58] Field of Search ............. 548/240, 237, 110; 546/283; 544/137; 71/77, 88, 94; 504/225, 252, 271, 193, 100, 191

[56] References Cited

FOREIGN PATENT DOCUMENTS 0148795 7/1985 European Pat. Off. ........... 548/237
0334120 9/1989 European Pat. Off. ........... 548/240

OTHER PUBLICATIONS

*Synthesis* 1986, 488–490, Shimizu et al., Synthesis of ... Dipolarophiles.

Vaughan et al., "5-Phenyl-2-isoxazoline-3-carboxylic Acid", *J. Org. Chem.* 25:1160–1164 (1960).

Matier et al., "Synthesis and Biological Properties of 5-Aryl-4H-1,2,4-thiadiazine 1,1-Dioxides", *Journal of Medicinal Chemistry* 17:549–552 (1974).

Kurosawa et al., "Acceleration of the Reductive Elimination Step in Pd-Catalysed Allylic Alkylation by Allylic Substrates", i J. Chem. Soc., Chem. Commun.:968–969 (1984).

CA 102:24531z The Reaction ... p-toluenesulfonic Acid. Shimizu et al., p. 686, 1985.

CA 106:138304r Synthesis of ... Dipolarophiles. Shimizu et al., p. 679, 1987.

CA 115:92254e Preparation of ... Safeners. Loeher et al., p. 765, 1991.

*Primary Examiner*—Mary C. Lee
*Assistant Examiner*—Joseph K. McKane
*Attorney, Agent, or Firm*—Curtis, Morris & Safford

[57] ABSTRACT

Compounds of the formula (I)

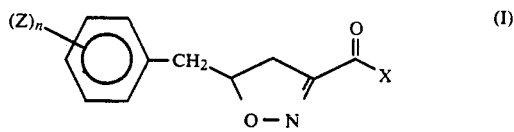

and their use as antidotes against the phytotoxicity of many herbicides used on crops, without diminishing the effect of the herbicide against weeds.

11 Claims, No Drawings

ISOXAZOLINES, THEIR PREPARATION, AND THEIR USE AS PLANT-PROTECTING AGENTS

The invention relates to safeners or antidotes which, in combination with herbicides, can reduce the phytotoxicity of the herbicides in crop plants.

The invention relates to plant-protecting isoxazolines of the formula (I) or salts thereof

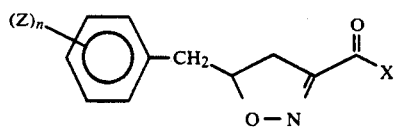

where
the Z radicals independently of one another are halogen, nitro, cyano, or alkyl, alkoxy, alkylthio or cycloalkyl, the four last-mentioned radicals being unsubstituted or monosubstituted or polysubstituted by alkoxy, hydroxyl or halogen, or furthermore are amino, mono- or dialkylamino, phenyl or phenoxy, phenyl and phenoxy independently of one another being unsubstituted or monosubstituted or polysubstituted by halogen or halogenoalkyl, or two adjacent substituents Z together are a divalent group of the formula —OCH$_2$O—, —S—CH$_2$—O— or —S—CH$_2$—S—, which group is unsubstituted or substituted by alkyl, n is an integer from 0 to 5,
X is hydroxyl or alkoxy, alkenyloxy, alkynyloxy, alkylthio or cycloalkoxy, the five last-mentioned radicals being unsubstituted or monosubstituted or polysubstituted by radicals from the group comprising alkoxy, alkylthio, mono- and dialkylamino, phenyl, substituted phenyl, cyano and halogen, or is furthermore phenoxy or substituted phenoxy, or is furthermore trialkylsilylmethoxy, a radical of the formula

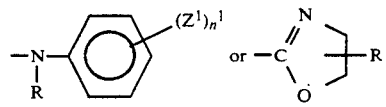

where R in each case is hydrogen or alkyl, Z$^1$ independently of Z has the meanings mentioned above in the case of Z, and n$^1$ is an integer from 0 to 5, or is furthermore amino, mono- or dialkylamino, cycloalkylamino, hydrazino, alkyl- or dialkylhydrazino, pyridino, morpholino, dimethylmorpholino, a radical of the formula

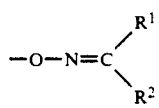

where R$^1$ and R$^2$ independently of one another are alkyl radicals or R$^1$ and R$^2$ together with the carbon atom linking them form a cycloalkyl radical, or is furthermore a radical of the formula

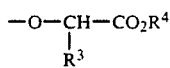

where R$^3$ and R$^4$ independently of one another are hydrogen or alkyl.

In formula (I), alkyl, alkoxy, haloalkyl, alkylamino and alkylthio radicals and the corresponding unsaturated and/or substituted radicals can be straight-chain or branched in each case. Alkyl radicals, also in the composed meanings such as alkoxy, haloalkyl etc., are methyl, ethyl, n- and i-propyl, n-, i-, t- and 2-butyl, the isomeric pentyl, hexyl, heptyl, octyl, nonyl, decyl, undecyl and dodecyl radicals, and the longer-chain fatty alkyl radicals which have up to 24 carbon atoms; C$_1$-C$_{12}$-alkyl radicals are preferred. Alkenyl and alkynyl radicals have the meanings of the unsaturated radicals which are possible and which correspond to the alkyl radicals, preferably (C$_2$-C$_{12}$)alkenyl and -alkynyl radicals. Halogen is fluorine, chlorine, bromine or iodine, preferably fluorine, chlorine or bromine, in particular fluorine or chlorine.

In the event that X=OH, the compounds of the formula (I) can form salts. The salts which can be employed according to the invention are those which can be used in agriculture. Suitable examples are metal salts such as alkali metal salts or alkaline earth metal salts, in particular sodium or potassium salts, ammonium salts or substituted ammonium salts which are monosubstituted to tetrasubstituted by alkyl and/or alkanol radicals having preferably up to 4 carbon atoms.

Formula (I) furthermore also embraces all stereoisomers and their mixtures, in particular also pure enantiomers and their mixtures (for example racemates). Stereoisomers can occur mainly when asymmetric carbon atoms or suitably substituted double bonds are present in the formula (I). An asymmetric carbon atom is the carbon atom bonded to the oxygen atom in the isoxazoline ring.

The plant-protecting compounds of the formula (I) according to the invention which are of particular interest are those in which
Z radicals independently of one another are halogen, nitro, cyano, (C$_1$-C$_4$)alkyl, (C$_1$-C$_4$)alkoxy, (C$_1$-C$_4$)-alkylthio, the alkyl, alkoxy and alkylthio groups being unsubstituted or monosubstituted or polysubstituted by halogen atoms, in particular fluorine or chlorine, or are (C$_3$-C$_6$)cycloalkyl which is unsubstituted or substituted by (C$_1$-C$_4$)alkyl, or are amino, (C$_1$-C$_4$)alkylamino, di(C$_1$-C$_4$)alkylamino, hydroxymethyl, (C$_1$-C$_4$)alkoxymethyl, phenyl or phenoxy, phenyl and phenoxy being unsubstituted or monosubstituted or polysubstituted by halogen or monosubstituted by trifluoromethyl or substituted by one or more halogen atoms and one trifluoromethyl, or two adjacent substituents Z are the divalent group —O—CH$_2$—O—, —S—CH$_2$—O— or —S—CH$_2$—S— and n is 0, 1, 2 or 3.

Particularly interesting agents according to the invention are those containing compounds of the formula (I) in which
X is hydroxyl, —OCH$_2$Si(CH$_3$)$_3$, (C$_3$-C$_6$)cycloalkoxy, phenyl(C$_1$-C$_6$)alkoxy, phenoxy, (C$_2$-C$_6$)alkenyloxy, (C$_2$-C$_6$)alkynyloxy, (C$_1$-C$_6$)alkoxy or (C$_1$-C$_6$)alkylthio, the alkoxy or alkylthio group being unsubstituted or monosubstituted or disubstituted by (C$_1$-C$_2$)alkoxy, mono- or di(C$_1$-C$_6$)alkylamino, (C$_1$-C$_2$)alkylthio, or cyano or monosubstituted or polysubstituted by halogen, or a radical of the formula

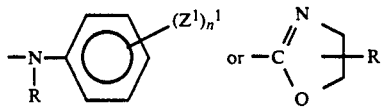

where R in each case is hydrogen or $(C_1-C_4)$alkyl, $Z^1$ has the meaning mentioned above in the case of Z, and $n^1$ is 0, 1, 2 or 3, or is furthermore amino, mono- or di$(C_1-C_4)$alkylamino, $(C_5-C_6)$cycloalkylamino, hydrazino, piperidino, morpholino or 2,6-dimethylmorpholino, a radical of the formula

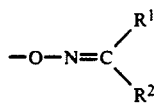

where $R^1$ and $R^2$ independently of one another are $(C_1-C_4)$-alkyl, or $R^1$ and $R^2$ together with the carbon atom linking them form a 5-, 6- or 7-membered cycloalkyl radical, or is a radical of the formula

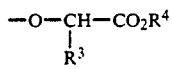

where $R^3$ and $R^4$ independently of one another are hydrogen or $(C_1-C_4)$alkyl.

Preferred compounds of the formula (I) according to the invention or salts thereof are those where
Z radicals independently of one another are halogen, in particular fluorine or chlorine, or nitro, $(C_1-C_4)$alkyl, $(C_1-C_4)$alkoxy or trifluoromethyl, and
n is 0, 1 or 2,
and those compounds of the formula (I) in which
X is hydroxyl, $(C_1-C_4)$alkoxy or a radical of the formula

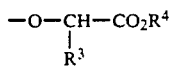

where $R^3$ is hydrogen or $CH_3$ and $R^4$ is hydrogen or $(C_1-C_4)$alkyl.

Particularly preferred compounds of the formula (I) according to the invention are those in which Z, n and X in each case have meanings which have been mentioned as being preferred.

The present invention also relates to a process for the preparation of the compounds of the formula (I) and salts thereof, which comprises reacting a compound of the formula (II)

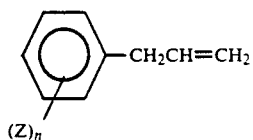

where $(Z)_n$ has the meanings given in formula (I), with a nitrile oxide of the formula (III)

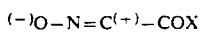                                    (III)

where X has the meaning given in formula (I).

Suitable solvents are unpolar organic solvents, for example ethers such as diethyl ether or THF.

The starting compounds of the formula (II) and (III) are known from the literature (cf. J. Org. Chem. 25, 1160 (1960); J. Med. Chem. 17 (1974), 549-552; J. Chem. Soc. Chem. Commun. 1984, 968-969; and the references mentioned therein) or can be prepared analogously to known compounds. In general, the nitrile oxides of the formula (III) are prepared in situ from 2-halo-2-hydroximinoacetic acid (derivatives) under the action of bases, and they are directly reacted with compound of the formula (II) already present in the reaction mixture. The reaction is preferably carried out at a temperature from $-15°$ C. to the boiling point of the solvent, in particular at room temperature.

The compounds of the formula (I) contain a center of asymmetry on the carbon atom which is bonded to the oxygen atom in the isoxazoline ring. Corresponding enantiomeric forms can be follow [sic] by customary methods, for example by racemate resolution. A racemate resolution is generally possible via diastereomeric salts of the compounds of the formula I in which X=OH, using optically active bases.

The compounds of the formula (I) reduce or prevent undesirable phytotoxic secondary effects, which can occur when herbicides are employed in crops.

The compounds of the formula (I) and the herbicidal active substances can be applied together or in succession in any desired sequence. The compounds of the formula (I) are then capable of lessening or completely eliminating noxious secondary effects of the herbicides in crop plants, without impairing the effectiveness of these herbicides towards noxious plants.

By virtue of this, the field of application of conventional plant protection agents can be widened to a very considerable extent. Such compounds which possess the property of protecting crop plants against phytotoxic damage by herbicides are called "antidotes" or "safeners".

Examples of herbicides whose phytotoxic secondary effects can be reduced by means of the compounds of the formula (I) are carbamates, thiocarbamates, haloacetanilides, substituted phenoxy-, naphthoxy-, phenoxyphenoxy-, benzyloxyphenoxy- and heteroaryloxyphenoxy-carboxylic acid derivatives as well as cyclohexanedione derivatives. Examples of heteroaryloxyphenoxycarboxylic acid derivatives are quinolyloxy-, quinoxalyloxy-, pyridyloxy-, benzoxazolyloxy- and benzothiazolyloxy-phenoxy-carboxylic acid esters. Preferred compounds are phenoxyphenoxy- and heteroaryloxyphenoxy-carboxylic acid esters. Suitable esters in this connection are, in particular, lower alkyl, alkenyl and alkynyl esters.

The following herbicides may be mentioned by way of example but without imposing any restriction:

A) Herbicides of the type of the $(C_1-C_4)$alkyl, $(C_2-C_4)$-alkenyl and $(C_3-C_4)$alkynyl phenoxyphenoxy-, benzylphenoxy- and heteroaryloxyphenoxy-carboxylates, such as
methyl 2-(4-(2,4-dichlorophenoxy)phenoxy)propionate,
methyl 2-(4-(4-bromo-2-chlorophenoxy)phenoxy)propionate,
methyl 2-(4-(4-trifluoromethylphenoxy)phenoxy)propionate,
methyl 2-(4-(2-chloro-4-trifluoromethylphenoxy)phenoxy)propionate,
methyl 2-(4-(2,4-dichlorobenzyl)phenoxy)propionate, ethyl 4-(4-(4-trifluoromethylphenoxy)phenoxy)pent-2-enoate,
ethyl 2-(4-(3,5-dichloropyridyl-2-oxy)phenoxy)propionate, propargyl 2-(4-(3,5-dichloropyridyl-2-oxy)phenoxy)propionate,
ethyl 2-(4-(6-chlorobenzoxazol-2-yloxy)phenoxy)propionate,
methyl 2-(4-(3-chloro-5-trifluoromethyl-2-pyridyloxy)phenoxy)propionate,
butyl 2-(4-(5-trifluoromethyl-1-2-pyridyloxy)phenoxy)propionate,
methyl 2-(4-(3-fluoro-5-chloropyridyl-2-oxy)phenoxy)propionate,
propargyl 2-(4-(3-fluoro-5-chloropyridyl-2-oxy)phenoxy)propionate,
methyl 2-(4-(6-chloro-2-quinoxalyloxy)phenoxy)propionate,
methyl 2-(4-(6-fluoro-2-quinoxalyloxy)phenoxy)propionate,
methyl 2-(4-(6-chloro-2-quinolyloxy)phenoxy)propionate, 5-methoxycarbonylmethyl 2-(4-(5-chloro-3-fluoropyridin-2-yloxy)phenoxy)thiopropionate,
B) Chloroacetanilide herbicides, such as
N-methoxymethyl-2,6-diethylchloroacetanilide,
N-(3′-methoxyprop-2′-yl)methyl-6-ethylchloroacetanilide,
N-(3-methyl-1,2,4-oxdiazol-5-ylmethyl)-2,6-dimethylchloroacetanilide,
C) Thiocarbamates, such as
S-ethyl N,N-dipropylthiocarbamate or
S-ethyl N,N-diisobutylthiocarbamate
D) Cyclohexanedione derivatives, such as
methyl 3-(1-allyloxyimino)butyl-4-hydroxy-6,6-dimethyl-2-oxocyclohex-3-enecarboxylate,
2-(N-ethoxybutyrimidoyl)-5-(2-ethylthiopropyl)-3-hydroxy-2-cyclohexen-1-one,
2-(N-ethoxybutyrimidoyl)-5-(2-phenylthiopropyl)-3-hydroxy-2-cyclohexen-1-one,
2-(1-allyloxyiminobutyl)-4-methoxycarbonyl-5,5-dimethyl-3-oxocyclohexenol,
2-(1-(3-chloroallyloxy)iminobutyl)-5-(2-ethylthio)propyl-3-hydroxycyclohex-2-enone,
2-(1-(ethoxyimino)butyl)-3-hydroxy-5-(thian-3-yl)cyclo-hex-2-enone or
2-(1-ethoxyiminopropyl)-5-(2,4,6-trimethylphenyl)-3-hydroxy-2-cyclohexen-1-one.

The ratio of safener:herbicide can vary within wide limits, preferably within the range of between 1:10 and 10:1, in particular between 2:1 and 1:10. The amounts of herbicide and safener which are ideal in each case depend on the type of the herbicide used or on the safener used as well as on the nature of the plant stand to be treated, and they can be determined for each individual case by appropriate experiments.

The safeners are mainly employed in particular in cereal crops (wheat, rye, barley, oats), rice, maize, sorghum, but also in cotton, sugar beet, sugar cane and soya bean.

Depending on their properties, the safeners of the formula (I) can be used for pre-treating the seed of the crop plant (seed treatment), or they can be incorporated in the seed furrows prior to sowing, or used together with the herbicide prior to, or after, plant emergence. Pre-emergence treatment includes both the treatment of the cropping area prior to sowing and treatment of the cropping areas where seed has been sown but growth of the crop plants has not yet taken place. Application together with the herbicide is preferred. Tank mixes or readymixes can be employed for this purpose.

The application rates which are required for the compounds of the formula (I) can vary within wide limits, depending on the indication and the herbicide used, and they generally vary between 0.01 and 10 kg of active These individual formulation types are known in principle and are described, for example, in:
Winnacker-Küchler, "Chemische Technologie [Chemical Technology]", Volume 7, C. Hauser Verlag Munich, 4th Ed., 1986; van Valkenburg, "Pesticides Formulations", Marcel Dekker N.Y., 2nd Ed. 1972-73; K. Martens, "Spray Drying Handbook", 3rd Ed. 1979, G. Goodwin Ltd. London.

The formulation auxiliaries required, such as inert materials, surfactants, solvents and other additives, are likewise known and are described, for example, in: Watkins, "Handbook of Insecticide Dust Diluents and Carriers", 2nd Ed., Darland Books, Caldwell, N.J.; H. V. Olphen, "Introduction to Clay Colloid Chemistry", 2nd Ed., J. Wiley & Sons, N.Y.; Marsden, "Solvents Guide", 2nd Ed., Interscience, N.Y. 1950; McCutcheon's, "Detergents and Emulsifiers Annual", MC Publ. Corp. Ridgewood, N.J.; Sisley and Wood, "Encyclopedia of Surface Active Agents", Chem. Publ. Co. Inc., N.Y. 1964; Schönfeldt, "Grenzflächenaktive Äthylenoxidaddukte" Surface-active Ethylene Oxide Adducts]", Wiss. Verlagsgesell., Stuttgart 1976; Winnacker-Küchler, "Chemische Technologie [Chemical Technology]", Volume 7, C. Hauser Verlag Munich, 4th Ed. 1986

Combinations with other pesticidally active substances, fertilizers and/or growth regulators may also be prepared on the basis of these formulations, for example in the form of a readymix or as a tank mix.

The invention therefore also relates to those agents which contain the compounds of the formula (I) according to the invention. These are mainly, on the one hand, plant-protecting agents which contain one or more compounds of the formula (I) and customary inert auxiliaries which correspond to the particular type of formulation, and, on the other hand, herbicidal agents which contain a combination of compounds of the formula (I) and one or more herbicides and customary auxiliaries which substance per hectare.

The present invention also relates to a method of protecting crop plants against phytotoxic secondary effects of herbicides, which comprises applying an effective amount of a compound of the formula (I) to the plants, seeds of the plants or the cropping area, prior to, after, or simultaneously with, the herbicide.

Moreover, the compounds according to the invention exhibit growth-regulating properties in crop plants. They engage in the plant metabolism in a regulating manner and can thus be employed for facilitating the harvest, for example by provoking desiccation, abscission and stunted growth. Moreover, they are also suitable for generally monitoring and inhibiting undesired vegetative growth, without at the same time destroying the plants. Inhibition of vegetative growth is very important in many monocotyledon and dicotyledon crops since lodging can be reduced, or completely inhibited, by this means.

The compounds of the formula (I) or their combination with one or more of the herbicides or groups of herbicides mentioned can be formulated in a variety of ways, as predetermined by the biological and/or chemiophysical parameters. The following possibilities are therefore suitable for formulation: wettable powders (WP), emulsifiable concentrates (EC), water-soluble powders (SP), water-soluble concentrates (SL), emulsions (EW), sprayable solutions, capsule suspensions (CS), dispersions on an oil or water base, suspoemulsions, suspension concentrates (SC), dusts (DP), oil-miscible solutions (OL), seed-treatment agents, granules (GR) in the form of microgranules, spray granules, coated granules and adsorption granules, granules for soil treatment or for application by broadcasting, water-soluble granules (SG), water-dispersible granules (WG), ULV formulations, microcapsules and waxes. correspond to the particular type of formulation.

Wettable powders are preparations which are uniformly dispersible in water and which, besides the active substance, also contain wetting agents, for example polyoxethylated alkylphenols, polyoxethylated fatty alcohols and fatty amines, fatty alcohol polyglycol ether sulfates, alkanesulfonates or alkylphenolsulfonates, and dispersing agents, for example sodium ligninsulfonate, sodium 2,2'-dinaphthylmethane-6,6'-disulfonate, sodium dibutylnaphthalenesulfonate, or alternatively sodium oleylmethyltaurinate, in addition to a diluent or inert substance. Emulsifiable concentrates are prepared by dissolving the active substance in an organic solvent, for example butanol, cyclohexanone, dimethylformamide, xylene and also higher-boiling aromatic compounds or hydrocarbons, with the addition of one or more emulsifiers. Examples of emulsifiers which can be used are: calcium salts of an alkylarylsulfonic acid, such as Ca dodecylbenzenesulfonate, or non-ionic emulsifiers, such as fatty acid polyglycol esters, alkylaryl polyglycol ethers, fatty alcohol polyglycol ethers, propylene oxide/ethylene oxide condensation products, alkyl polyethers, sorbitan fatty acid esters, polyoxyethylene sorbitan fatty acid esters or polyoxyethylene sorbitol esters.

Dusting agents can be obtained by grinding the active substance with finely divided solid substances, for example talc or natural clays, such as kaolin, bentonite, pyrophillite [sic], or diatomaceous earth.

Granules can be produced either by spraying the active substance onto adsorptive, granulated inert material or by applying active substance concentrates onto the surface of carriers, such as sand, kaolinites or granulated inert material, by means of binders, for example polyvinyl alcohol, sodium polyacrylate or, alternatively, mineral oils. Suitable active substances can also be granulated in the manner which is conventional for the production of fertilizer granules, if desired in a mixture with fertilizers.

In general, the agrochemical preparations contain 0.1 to 99% by weight, in particular 0.1 to 95% by weight, of active substance of the formula (I), or of active-substance-mixture antidote/herbicide, 1 to 99.9% by weight, in particular 5 to 99.8% by weight, of a solid or liquid additive, and 0 to 25% by weight, in particular 0.1 to 25% by weight, of a surfactant.

The concentration of active substance in wettable powders is, for example, about 10 to 90% by weight, the remainder to 100% by weight is composed of conventional formulation components. In the case of emulsifiable concentrates, the concentration of active substance can be about 1 to 80% by weight, preferably 5 to 80% by weight. Formulations in the form of dusts usually contain 1 to 25% by weight, preferably 5 to 20% by weight of active substance, sprayable solutions about 0.2 to 25% by weight, preferably 2 to 20% by weight of active substance. In the case of granules, such as water-dispersible granules, the active substance content depends partly on whether the active compound is liquid or solid. In general, the water-dispersible granules contain between 10 and 90% by weight of active substance.

In addition, the active substance formulations mentioned contain, if appropriate, the adhesives, wetting agents, dispersing agents, emulsifiers, penetrants, solvents, fillers or carriers which are conventional in each case.

For use, the concentrates, present in commercially available form, are diluted, if appropriate, in a customary manner, for example using water in the case of wettable powders, emulsifiable concentrates, dispersions and water-dispersible granules. Preparations in the form of dusts, soil granules or granules for broadcasting, and also sprayable solutions are usually not further diluted with other inert substances before use.

The application rate required for the compounds of the formula (I) varies with the external conditions, such as, inter alia, temperature, humidity, and the nature of the herbicide used. It can vary within wide limits, for example between 0.005 and 10.0 kg/ha or more of active ingredient, preferably, however, it is between 0.01 and 5 kg/ha.

The examples which follow serve to illustrate the invention:

A. Formulation Examples a) A dusting agent is obtained by mixing 10 parts by weight of a compound of the formula (I) and 90 parts by weight of talc or inert substance and comminuting the mixture in a hammer mill.

b) A wettable powder which is readily dispersible in water is obtained by mixing 25 parts by weight of a compound of the formula (I), 64 parts by weight of kaolin-containing quartz as the inert substance, 10 parts by weight of potassium ligninsulfonate and 1 part by weight of sodium oleoylmethyltaurinate as the wetting and dispersing agent, and grinding the mixture in a pinned disk-mill.

c) A dispersion concentrate which is readily dispersible in water is obtained by mixing 20 parts by weight of a compound of the formula (I) with 6 parts by weight of alkylphenol polyglycol ether (®Triton X 207), 3 parts by weight of isotridecanol polyglycol ether (8 EO) and 71 parts by weight of paraffinic mineral oil (boiling range, for example, about 255° to above 277° C.), and grinding the mixture in a ball mill to a fineness of below 5 microns.

d) An emulsifiable concentrate is obtained from 15 parts by weight of a compound of the formula (I), 75 parts by weight of cyclohexanone as the solvent and 10 parts by weight of oxyethylated nonylphenol as the emulsifier.

e) Water-dispersible granules are obtained by mixing 75 parts by weight of a compound of the formula I,
10 parts by weight of calcium lignin sulfonate,
5 parts by weight of sodium lauryl sulfate,
3 parts by weight of polyvinyl alcohol and
7 parts by weight of kaolin, grinding the mixture on a pinned disk-mill, and granulating the powder in a fluidized bed by spraying on water as the granulation liquid.

f) Water-dispersible granules are also obtained by homogenizing and precomminuting, on a colloid mill,

| |
|---|
| 25 parts by weight of a compound of the formula (I), |
| 5 parts by weight of sodium 2,2'-dinaphthyl methane-6,6'-disulfonate, |
| 2 parts by weight of sodium oleoylmethyltaurinate, |
| 1 part by weight of polyvinyl alcohol, |
| 17 parts by weight of calcium carbonate and |
| 50 parts by weight of water, | subsequently grinding the mixture on a bead mill, and atomizing and drying the resulting suspension in a spray tower by means of a single-fluid jet.

B) Chemical Examples

Methyl 5-(2,4-dichlorobenzyl)-2-isoxazoline-3-carboxylate (Example No. 93)

18.8 ml of triethylamine are added dropwise to 10.7 g of 2,4-dichloro-1-allylbenzene in 270 ml of ether. A solution of 20.55 g of ethyl 2-chloro-2-hydroximinoacetate in 270 ml of ether is subsequently slowly added dropwise in the course of 5 hours. After this, the mixture is stirred for 24 hours and extracted with water, the ether phase is dried, and ether is distilled off. In this way, 35.5 g (98% of theory) of the above-named product of refractive index $n_D^{25} = 1.534$ are obtained.

Ethyl 2-chloro-2-hydroximinoacetate
(Starting material for Example No. 93)

69.8 g of glycine ethyl ester hydrochloride are initially introduced into 120 ml of water and 41 ml of concentrated hydrochloric acid. 38 g of $NaNO_2$ in 60 ml of water are then added dropwise at $-10°$ C. in the course of 1 hour. After half an hour, a further 42.5 ml of concentrated hydrochloric acid are added, and then, in the course of 1 hour, a further 38 g of $NaNO_2$ in 60 ml of water. Stirring is continued for 1 hour at $-10°$ C. The mixture is subsequently extracted with ether, and the ether phase is washed several times with water. The ether is distilled off, and the crystals are dried. In this way, 38 g (50% of theory) of ethyl 2-chloro-2-hydroximinoacetate of a melting point of $81°-82°$ C. are obtained.

In Table I below, the abovementioned Example is listed together with further examples which can be prepared in an analogous manner.

The analogous isoxazoline carboxylic acids can be prepared from the corresponding esters, or the isoxazoline esters can be prepared, if desired, from the corresponding carboxylic acids, by methods known in principle.

TABLE I

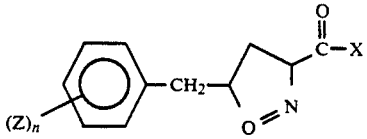

| No. | $(Z)_n$ | X | M.p. $(n_D^{20})$ |
|---|---|---|---|
| 1 | n = 0 | $-O-C_2H_5$ | Oil |
| 2 | " | $-OCH_3$ | 75-77° C. |
| 3 | " | $-OH$ | 128° C. |
| 4 | " | $-OC_3H_7$ | (1.5199) |
| 5 | " | $-OCH(CH_3)_2$ | |
| 6 | " | $-OC_4H_9$ | |
| 7 | " | $-OCH_2CH(CH_3)_2$ | |
| 8 | " | $-OCH_2CO_2CH_3$ | |
| 9 | " | $-OCH_2CO_2C_2H_5$ | |
| 10 | " | $-OCH(CH_3)CO_2C_2H_5$ | (1.5091) |
| 11 | " | $-NH-NH_2$ | |
| 12 | " | $-OCH_2-C_6H_5$ | |
| 13 | " | $-N(CH_3)_2$ | |
| 14 | " | $-NH_2$ | |
| 15 | " | $-OCH(CH_3)CO_2CH_3$ | |
| 16 | " | $-NHC_6H_5$ | |
| 17 | " | $-OCH_2CH=CH_2$ | |
| 18 | " | $-OCH_2C\equiv CH$ | |
| 19 | " | $-O^-K^+$ | |
| 20 | " | $-O^-Na^+$ | |
| 21 | " | $-O^-NH_4$ | |
| 22 | " | $-OCH_2Si(CH_3)_3$ | |
| 23 | " | $-OC_6H_5$ | |
| 24 | 4-F | $-O-C_2H_5$ | Oil |
| 25 | " | $-OCH_3$ | |
| 26 | " | $-OH$ | 138-140° C. |
| 27 | " | $-OC_3H_7$ | |
| 28 | " | $-OCH(CH_3)_2$ | |
| 29 | " | $-OC_4H_9$ | |
| 30 | " | $-OCH_2CH(CH_3)_2$ | |
| 31 | " | $-OCH_2CO_2CH_3$ | |
| 32 | " | $-OCH_2CO_2C_2H_5$ | |
| 33 | " | $-OCH(CH_3)CO_2C_2H_5$ | |
| 34 | " | $-NH-NH_2$ | Oil |
| 35 | " | $-OCH_2-C_6H_5$ | |
| 36 | " | $-N(CH_3)_2$ | |
| 37 | " | $-NH_2$ | |
| 38 | " | $-OCH(CH_3)CO_2CH_3$ | |
| 39 | " | $-NHC_6H_5$ | |
| 40 | " | $-OCH_2CH=CH_2$ | |
| 41 | " | $-OCH_2C\equiv CH$ | |
| 42 | " | $-O^-K^+$ | |
| 43 | " | $-O^-Na^+$ | |

TABLE I-continued

[Structure: (Z)n-phenyl-CH2-CH(O-N=)-CH2-C(=O)-X, with oxazoline-like ring]

| No. | (Z)$_n$ | X | M.p. (n$_D^{20}$) |
|---|---|---|---|
| 44 | " | —O$^-$NH$_4$ | |
| 45 | " | —OCH$_2$Si(CH$_3$)$_3$ | |
| 46 | " | —OC$_6$H$_5$ | |
| 47 | 4-Cl | —O—C$_2$H$_5$ | Oil |
| 48 | " | —OCH$_3$ | 92° C. |
| 49 | " | —OH | 140° C. |
| 50 | " | —OC$_3$H$_7$ | (1.5075) |
| 51 | " | —OCH(CH$_3$)$_2$ | |
| 52 | " | —OC$_4$H$_9$ | |
| 53 | " | —OCH$_2$CH(CH$_3$)$_2$ | |
| 54 | " | —OCH$_2$CO$_2$CH$_3$ | |
| 55 | " | —OCH$_2$CO$_2$C$_2$H$_5$ | |
| 56 | " | —OCH(CH$_3$)CO$_2$C$_2$H$_5$ | (1.514) |
| 57 | " | —NH—NH$_2$ | |
| 58 | " | —OCH$_2$—C$_6$H$_5$ | |
| 59 | " | —N(CH$_3$)$_2$ | |
| 60 | " | —NH$_2$ | |
| 61 | " | —OCH(CH$_3$)CO$_2$CH$_3$ | |
| 62 | " | —NHC$_6$H$_5$ | |
| 63 | " | —OCH$_2$CH=CH$_2$ | |
| 64 | " | —OCH$_2$C≡CH | |
| 65 | " | —O$^-$K$^+$ | |
| 66 | " | —O$^-$Na$^+$ | |
| 67 | " | —O$^-$NH$_4$ | |
| 68 | " | —OCH$_2$Si(CH$_3$)$_3$ | |
| 69 | " | —OC$_6$H$_5$ | |
| 70 | 2-Cl | —O—C$_2$H$_5$ | (1.526) |
| 71 | " | —OCH$_3$ | (1.547) |
| 72 | " | —OH | 80° C. |
| 73 | " | —OC$_3$H$_7$ | (1.533) |
| 74 | " | —OCH(CH$_3$)$_2$ | |
| 75 | " | —OC$_4$H$_9$ | (1.523) |
| 76 | " | —OCH$_2$CH(CH$_3$)$_2$ | |
| 77 | " | —OCH$_2$CO$_2$CH$_3$ | |
| 78 | " | —OCH$_2$CO$_2$C$_2$H$_5$ | |
| 79 | " | —OCH(CH$_3$)CO$_2$C$_2$H$_5$ | |
| 80 | " | —NH—NH$_2$ | |
| 81 | " | —OCH$_2$—C$_6$H$_5$ | |
| 82 | " | —N(CH$_3$)$_2$ | |
| 83 | " | —NH$_2$ | |
| 84 | " | —OCH(CH$_3$)CO$_2$CH$_3$ | |
| 85 | " | —NHC$_6$H$_5$ | |
| 86 | " | —OCH$_2$CH=CH$_2$ | |
| 87 | " | —OCH$_2$C≡CH | |
| 88 | " | —O$^-$K$^+$ | |
| 89 | " | —O$^-$Na$^+$ | |
| 90 | " | —O$^-$NH$_4$ | |
| 91 | " | —OCH$_2$Si(CH$_3$)$_3$ | |
| 92 | " | —OC$_6$H$_5$ | |
| 93 | 2,4-Cl$_2$ | —O—C$_2$H$_5$ | (1.534) |
| 94 | " | —OCH$_3$ | (1.544) |
| 95 | " | —OH | 40° C. |
| 96 | " | —OC$_3$H$_7$ | |
| 97 | " | —OCH(CH$_3$)$_2$ | |
| 98 | " | —OC$_4$H$_9$ | |
| 99 | " | —OCH$_2$CH(CH$_3$)$_2$ | |
| 100 | " | —OCH$_2$CO$_2$CH$_3$ | |
| 101 | " | —OCH$_2$CO$_2$C$_2$H$_5$ | |
| 102 | " | —OCH(CH$_3$)CO$_2$C$_2$H$_5$ | |
| 103 | " | —NH—NH$_2$ | Oil |
| 104 | " | —OCH$_2$—C$_6$H$_5$ | |
| 105 | " | —N(CH$_3$)$_2$ | |
| 106 | " | —NH$_2$ | |
| 107 | " | —OCH(CH$_3$)CO$_2$CH$_3$ | |
| 108 | " | —NHC$_6$H$_5$ | |
| 109 | " | —OCH$_2$CH=CH$_2$ | |
| 110 | " | —OCH$_2$C≡CH | |
| 111 | " | —O$^-$K$^+$ | |
| 112 | " | —O$^-$Na$^+$ | |
| 113 | " | —O$^-$NH$_4$ | |
| 114 | " | —OCH$_2$Si(CH$_3$)$_3$ | |
| 115 | " | —OC$_6$H$_5$ | |
| 116 | 2-OCH$_3$ | —O—C$_2$H$_5$ | Oil |

TABLE I-continued

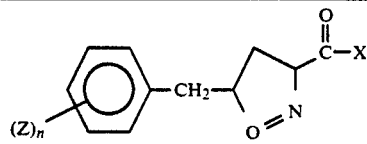

| No. | (Z)$_n$ | X | M.p. (n$_D^{20}$) |
|---|---|---|---|
| 117 | " | —OCH$_3$ | |
| 118 | " | —OH | |
| 119 | " | —OC$_3$H$_7$ | |
| 120 | " | —OCH(CH$_3$)$_2$ | |
| 121 | " | —OC$_4$H$_9$ | |
| 122 | " | —OCH$_2$CH(CH$_3$)$_2$ | |
| 123 | " | —OCH$_2$CO$_2$CH$_3$ | |
| 124 | " | —OCH$_2$CO$_2$C$_2$H$_5$ | |
| 125 | " | —OCH(CH$_3$)CO$_2$C$_2$H$_5$ | |
| 126 | " | —NH—NH$_2$ | |
| 127 | " | —OCH$_2$—C$_6$H$_5$ | |
| 128 | " | —N(CH$_3$)$_2$ | |
| 129 | " | —NH$_2$ | |
| 130 | " | —OCH(CH$_3$)CO$_2$CH$_3$ | |
| 131 | " | —NHC$_6$H$_5$ | |
| 132 | " | —OCH$_2$CH=CH$_2$ | |
| 133 | " | —OCH$_2$C≡CH | |
| 134 | " | —O$^-$K$^+$ | |
| 135 | " | —O$^-$Na$^+$ | |
| 136 | " | —O$^-$NH$_4$ | |
| 137 | " | —OCH$_2$Si(CH$_3$)$_3$ | |
| 138 | " | —OC$_6$H$_5$ | |
| 139 | 2-CH$_3$, 4-Cl | —O—C$_2$H$_5$ | |
| 140 | " | —OCH$_3$ | |
| 141 | " | —OH | |
| 142 | " | —OC$_3$H$_7$ | |
| 143 | " | —OCH(CH$_3$)$_2$ | |
| 144 | " | —OC$_4$H$_9$ | |
| 145 | " | —OCH$_2$CH(CH$_3$)$_2$ | |
| 146 | " | —OCH$_2$CO$_2$CH$_3$ | |
| 147 | " | —OCH$_2$CO$_2$C$_2$H$_5$ | |
| 148 | " | —OCH(CH$_3$)CO$_2$C$_2$H$_5$ | |
| 149 | " | —NH—NH$_2$ | |
| 150 | " | —OCH$_2$—C$_6$H$_5$ | |
| 151 | " | —N(CH$_3$)$_2$ | |
| 152 | " | —NH$_2$ | |
| 153 | " | —OCH(CH$_3$)CO$_2$CH$_3$ | |
| 154 | " | —NHC$_6$H$_5$ | |
| 155 | " | —OCH$_2$CH=CH$_2$ | |
| 156 | " | —OCH$_2$C≡CH | |
| 157 | " | —O$^-$K$^+$ | |
| 158 | " | —O$^-$Na$^+$ | |
| 159 | " | —O$^-$NH$_4$ | |
| 160 | " | —OCH$_2$Si(CH$_3$)$_3$ | |
| 161 | " | —OC$_6$H$_5$ | |
| 162 | 2,3,4,5,6-F$_5$ | —O—C$_2$H$_5$ | 89° C. |
| 163 | " | —OCH$_3$ | 121° C. |
| 164 | " | —OH | |
| 165 | " | —OC$_3$H$_7$ | |
| 166 | " | —OCH(CH$_3$)$_2$ | |
| 167 | " | —OC$_4$H$_9$ | |
| 168 | " | —OCH$_2$CH(CH$_3$)$_2$ | |
| 169 | " | —OCH$_2$CO$_2$CH$_3$ | |
| 170 | " | —OCH$_2$CO$_2$C$_2$H$_5$ | |
| 171 | " | —OCH(CH$_3$)CO$_2$C$_2$H$_5$ | |
| 172 | " | —NH—NH$_2$ | |
| 173 | " | —OCH$_2$—C$_6$H$_5$ | |
| 174 | " | —N(CH$_3$)$_2$ | |
| 175 | " | —NH$_2$ | |
| 176 | " | —OCH(CH$_3$)CO$_2$CH$_3$ | |
| 177 | " | —NHC$_6$H$_5$ | |
| 178 | " | —OCH$_2$CH=CH$_2$ | |
| 179 | " | —OCH$_2$C≡CH | |
| 180 | " | —O$^-$K$^+$ | |
| 181 | " | —O$^-$Na$^+$ | |
| 182 | " | —O$^-$NH$_4$ | |
| 183 | " | —OCH$_2$Si(CH$_3$)$_3$ | |
| 184 | " | —OC$_6$H$_5$ | |
| 185 | 3,4-O—CH$_2$—O— | —O—C$_2$H$_5$ | (1.541) |
| 186 | " | —OCH$_3$ | 102° C. |
| 187 | " | —OH | 147–149° C. |
| 188 | " | —OC$_3$H$_7$ | (1.516) |
| 189 | " | —OCH(CH$_3$)$_2$ | |

TABLE I-continued

| No. | (Z)ₙ | X | M.p. (n$_D^{20}$) |
|---|---|---|---|
| 190 | '' | —OC₄H₉ | (1.528) |
| 191 | '' | —OCH₂CH(CH₃)₂ | |
| 192 | '' | —OCH₂CO₂CH₃ | |
| 193 | '' | —OCH₂CO₂C₂H₅ | |
| 194 | '' | —OCH(CH₃)CO₂C₂H₅ | |
| 195 | '' | —NH—NH₂ | |
| 196 | '' | —OCH₂—C₆H₅ | |
| 197 | '' | —N(CH₃)₂ | |
| 198 | '' | —NH₂ | |
| 199 | '' | —OCH(CH₃)CO₂CH₃ | |
| 200 | '' | —NHC₆H₅ | |
| 201 | '' | —OCH₂CH=CH₂ | |
| 202 | '' | —OCH₂C≡CH | |
| 203 | '' | —O⁻K⁺ | |
| 204 | '' | —O⁻Na⁺ | |
| 205 | '' | —O⁻NH₄ | |
| 206 | '' | —OCH₂Si(CH₃)₃ | |
| 207 | '' | —OC₆H₅ | |
| 208 | 4-CF₃ | —OCH₃ | |
| 209 | 2-CF₃ | —OCH₃ | |
| 210 | 4-CF₃ | —OC₂H₅ | |
| 211 | 2-CF₃ | —OC₂H₅ | |
| 213 | 4-CF₃ | —OCH₂CO—OCH₃ | |
| 214 | 2-CF₃ | —OCH(CH₃)COOC₂H₅ | |
| 215 | 2-OCHF₂ | —OCH₃ | |
| 216 | '' | —OC₂H₅ | |
| 217 | '' | —OCH₂CO₂CH₃ | |
| 218 | 4-OCHF₂ | —OCH(CH₃)CO₂C₂H₅ | |
| 219 | '' | —OCH₃ | |
| 220 | '' | —OC₂H₅ | |
| 221 | 3-CF₃ | —OCH₃ | |
| 222 | 3-F | —OCH₃ | |
| 223 | 3-Cl | —OC₂H₅ | |
| 224 | 3,5-Cl₂ | —OH | |
| 225 | 3,5-F₂ | —OCH₃ | |
| 226 | 2-OCF₃ | —OCH₃ | |
| 227 | '' | —OC₂H₅ | |
| 228 | '' | —OCH₂CO₂CH₃ | |
| 229 | 4-OCF₃ | —OCH₃ | |
| 230 | '' | —OC₂H₅ | |
| 231 | '' | —OC₄H₉ | |
| 232 | 3-OCF₃ | —OCH₃ | |
| 233 | 2-SCH₃ | —OCH₃ | |
| 234 | 3-SCH₃ | —OCH₃ | |
| 235 | 4-SCH₃ | —OCH₃ | |
| 236 | 2-SC₂H₅ | —OCH₃ | |
| 237 | 3-SC₂H₅ | —OCH₃ | |
| 238 | 4-SC₂H₅ | —OCH₃ | |
| 239 | 2-CH₂CH₂OH | —OCH₃ | |
| 240 | 4-CH₂CH₂OH | —OCH₃ | |
| 241 | 2-CH₂CH₂OH | —OCH₃ | |
| 242 | 2-OCH₂CH₂OH | —OCH₃ | |
| 243 | 3-OCH₂CH₂OH | —OCH₃ | |
| 244 | 4-OCH₂CH₂OH | —OCH₃ | |
| 245 | 2-OCH₂CH₂OCH₃ | —OCH₃ | |
| 246 | 4-OCH₂CH₂OCH₃ | —OCH₃ | |
| 247 | 2-N(CH₃)₂ | —OCH₃ | |
| 248 | 3-N(C₂H₅)₂ | —OCH₃ | |
| 249 | 4-N(CH₃)₂ | —OCH₃ | |
| 250 | 4-NO₂ | —OCH₃ | |
| 251 | '' | —OC₂H₅ | |
| 252 | 2,4-(NO₂)₂ | —OCH₃ | |
| 252 | 2-NO₂ | —OCH₃ | |
| 254 | 3-NO₂ | —OCH₃ | |
| 255 | 2-CN | —OCH₃ | |
| 256 | 3-CN | —OCH₃ | |
| 257 | 4-CN | —OCH₃ | |
| 258 | 2-CN, 4-Cl | —OCH₃ | |
| 259 | 2-Cl, 4-CN | —OCH₃ | |
| 260 | 2-CH₃, 4-CN | —OCH₃ | |
| 261 | 4-Cyclo-C₆H₁₁ | —OCH₃ | |
| 262 | 4-Cyclo-C₅H₉ | —OCH₃ | |
| 263 | 4-C₆H₅ | —OCH₃ | |

TABLE I-continued

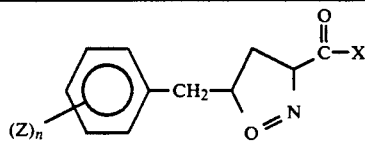

| No. | (Z)$_n$ | X | M.p. (n$_D^{20}$) |
|---|---|---|---|
| 264 | 4-OC$_6$H$_5$ | —OCH$_3$ | |
| 265 | 4-(2,4-C$_6$H$_3$Cl$_2$) | —OCH$_3$ | |
| 266 | 4-OC$_6$H$_3$Cl$_2$(2,4) | —OCH$_3$ | |
| 267 | 4-(2-CF$_3$—C$_6$H$_4$) | —OCH$_3$ | |
| 268 | 4-(4-CF$_3$—C$_6$H$_4$) | —OCH$_3$ | |
| 269 | 4-(2-CF$_3$—C$_6$H$_4$—O—) | —OCH$_3$ | |
| 270 | 4-(4-CF$_3$—C$_6$H$_4$—O—) | —OCH$_3$ | |
| 271 | 4-CH$_3$ | —OC$_2$H$_5$ | (1.505) |

C. Biological Examples

Example 1

Wheat and barley were grown in the greenhouse in plastic pots until they had reached the 3–4 leaf stage and then treated post-emergence with compounds and herbicides according to the invention. For this purpose, the herbicides and the compounds of the formula (I) were applied in the form of aqueous suspensions or emulsions at an application rate of 800 l of water/ha (converted). 3–4 weeks after the treatment, the plants were scored visually for any type of damage by the herbicides applied, and the extent of sustained growth inhibition was considered as particularly important. For the assessment, percentages in comparison with untreated controls were used.

The results from Table II demonstrate that the compounds according to the invention are capable of effectively reducing severe herbicide damage on crop plants.

Even when the herbicides are applied at substantial overdoses, the severe damage which occurs in the crop plants is markedly reduced, and lesser damage is compensated for completely. Mixtures of herbicides and compounds according to the invention are therefore outstandingly suitable for selectively controlling weeds in cereal crops.

TABLE II

| Safener action of the compounds according to the invention | | |
|---|---|---|
| Herbicide (H) + Safener No. | Dose in kg of a.i./ha | Damage to crop plants (%) |
| | | TRAE / HOVU |
| H | 2.0 | 80 / — |
| | 0.2 | — / 85–90 |
| H + 1 | 2.0 + 1.25 | 20 / — |
| H + 1 | 0.2 + 1.25 | — / 30 |
| H + 3 | 2.0 + 1.25 | 25 / — |
| H + 3 | 0.2 + 1.25 | — / 35 |
| H + 2 | 0.2 + 1.25 | — / 40 |
| H + 4 | " | — / 40 |
| H + 10 | " | — / 40 |
| H + 24 | " | — / 50 |
| H + 47 | " | — / 40 |
| H + 49 | " | — / 50 |
| H + 26 | " | — / 40 |
| H + 70 | " | — / 18 |
| H + 71 | " | — / 20 |
| H + 72 | " | — / 20 |
| H + 73 | " | — / 28 |
| H + 75 | " | — / 20 |
| H + 94 | " | — / 10 |
| H + 95 | " | — / 50 |

Abbreviations:
TRAE = *Triticum aestivum* (wheat)
HOVU = *Hordeum vulgare* (barley)
a.i. = Active ingredient (i.e. based on the pure active substance)
H = Ethyl 2-(4-(6-chlorobenzoxazol-2-yloxy)phenoxy-propionate (fenoxaprop-ethyl)
Safener No. = see No. of the preparation example from Table 1

We claim:

1. A compound of the formula (I) or a salt thereof

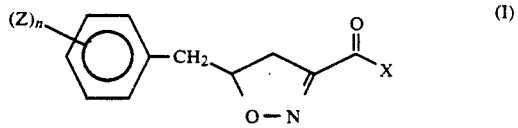

where
the Z radicals independently of one another are halogen, nitro, cyano, or alkyl, alkoxy, alkylthio or cycloalkyl, the four last-mentioned radicals being unsubstituted or monosubstituted or polysubstituted by alkoxy, hydroxyl or halogen, or furthermore are amino, mono- or dialkylamino, phenyl or phenoxy, phenyl and phenoxy independently of one another being unsubstituted or monosubstituted or polysubstituted by halogen or halogenoalkyl, or two adjacent substituents Z together are a divalent group of the formula —OCH$_2$O—, —S—CH$_2$—O— or —S—CH$_2$—S—, which group is unsubstituted or substituted by alkyl,
n is an integer from 0 to 5,
X is hydroxyl or alkoxy, alkenyloxy, alkynyloxy, alkylthio or cycloalkoxy, the five last-mentioned radicals being unsubstituted or monosubstituted or polysubstituted by radicals from the group comprising alkoxy, alkylthio, mono- and dialkylamino, phenyl, cyano and halogen, or is furthermore phenoxy, or is furthermore trialkylsilylmethoxy, a radical of the formula

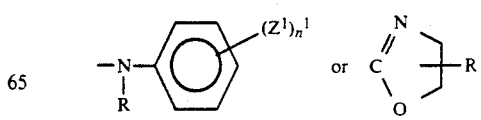

where R in each case is hydrogen or alkyl, $Z^1$ independently of Z has the meanings mentioned above in the case of Z, and $n^1$ is an integer from 0 to 5, or is furthermore amino, mono- or dialkylamino, cycloalkylamino, hydrazino, alkyl- or dialkylhydrazino, pyridino, morpholino, dimethylmorpholino, a radical of the formula

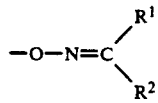

where $R^1$ and $R^2$ independently of one another are alkyl radicals or $R^1$ and $R^2$ together with the carbon tom linking them form a cycloalkyl radical, or is furthermore a radical of the formula

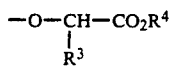

where $R^3$ and $R^4$ independently of one another are hydrogen or alkyl, with the exception of a compound of formula (I) in which n is zero and X is a radical of the formula

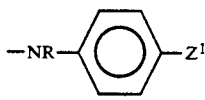

in which R is hydrogen, and $Z^1$ is hydrogen or chlorine.

2. A compound or a salt thereof as claimed in claim 1, wherein, in formula (I),

Z radicals independently of one another are halogen, nitro, cyano, $(C_1-C_4)$alkyl, $(C_1-C_4)$alkoxy, $(C_1-C_4)$-alkylthio, the alkyl, alkoxy and alkylthio groups being unsubstituted or monosubstituted or poly-substituted by halogen atoms, in particular fluorine or chlorine, or are $(C_3-C_6)$cycloalkyl which is unsubstituted or substituted by $(C_1-C_4)$alkyl, or are amino, $(C_1-C_4)$alkylamino, di$(C_1-C_4)$alkylamino, hydroxymethyl, $(C_1-C_4)$alkoxymethyl, phenyl or phenoxy, phenyl and phenoxy being unsubstituted or monosubstituted or polysubstituted by halogen or monosubstituted by trifluoromethyl or substituted by one or more halogen atoms and one trifluoromethyl, or two adjacent substituents Z are the divalent group —O—$CH_2$—O—, —S—$CH_2$—O— or —S—$CH_2$—S— and n is 0, 1, 2 or 3.

3. A compound or a salt thereof as claimed in claim 1 wherein

X is hydroxyl, —$OCH_2Si(CH_3)_3$, $(C_3-C_6)$cycloalkoxy, phenyl$(C_1-C_6)$alkoxy, phenoxy, $(C_2-C_6)$alkenyloxy, $(C_2-C_6)$alkynyloxy, $(C_1-C_6)$alkoxy or $(C_1-C_6)$alkylthio, the alkoxy or alkylthio group being unsubstituted or monosubstituted or disubstituted by $(C_1-C_2)$alkoxy, mono- or di$(C_1-C_6)$alkylamino, $(C_1-C_2)$alkylthio, or cyano or monosubstituted or polysubstituted by halogen, or a radical of the formula

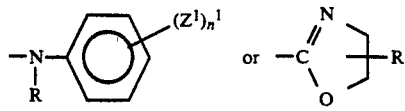

where R in each case is hydrogen or $(C_1-C_4)$alkyl, $Z^1$ has the meaning mentioned above in the case of Z, and n is 0, 1, 2 or 3, or is furthermore amino, mono- or di$(C_1-C_4)$alkylamino, $(C_5-C_6)$cycloalkylamino, hydrazino, piperidino, morpholino or 2,6-dimethylmorpholino, a radical of the formula

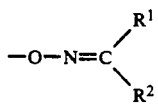

where $R^1$ and $R^2$ independently of one another are $(C_1-C_4)$alkyl, or $R^1$ and $R^2$ together with the carbon a linking them form a 5-, 6- or 7-membered cycloalkyl radical, or is a radical of the formula

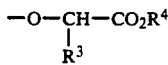

where $R^3$ and $R^4$ independently of one another are hydrogen or $(C_1-C_4)$alkyl.

4. A compound or a salt thereof as claimed in claim 1, wherein

Z radicals independently of one another are halogen, in particular fluorine or chlorine, or nitro, $(C_1-C_4)$alkyl, $(C_1-C_4)$alkoxy or trifluoromethyl, and
n is 0, 1 or 2, and
X is hydroxyl, $(C_1-C_4)$alkoxy or a radical of the formula

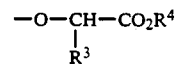

where $R^3$ is hydrogen or $CH_3$ and $R^4$ is hydrogen or $(C_1-C_4)$alkyl.

5. A plant-protecting agent which contains a compound of the formula (I), or a salt thereof, as claimed in claim 1, and inert additives.

6. A selective herbicidal agent which contains a herbicide, in combination with a compound of the formula, (I), or a salt thereof, which is as defined in claim 1.

7. An agent as claimed in claim 6, which contains, as the herbicide, an active substance from the group comprising the carbamates, thiocarbamates, haloacetanilides, substituted phenoxy-, naphthoxy-, phenoxyphenoxy-, benzyloxyphenoxy- and heteroaryloxyphenoxy-carboxylic acid derivatives and cyclohexanedione derivatives.

8. A method of controlling undesired plants in crops, which comprises applying a herbicide in combination with a compound of the formula (I), or a salt thereof, as defined in claim 1, to the plants, seeds of the plants or the cropping area.

9. A method for protecting crop plants against phytotoxic secondary effects of a herbicide, wherein a herbicide is applied in combination with a compound of the formula (I), or a salt thereof, as defined in claim 1, to the plants, seeds of the plants or the cropping area.

10. A method of controlling undesired plants in crops, which comprises applying to the plants, seeds of the plants or the cropping area, a herbicide in combination with a compound of the formula (I) or a salt thereof

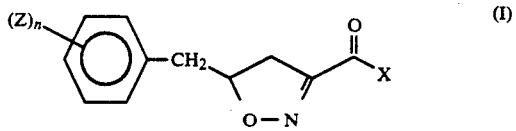

where the Z radicals independently of one another are halogen, nitro, cyano, or alkyl, alkoxy, alkylthio or cycloalkyl, the four last-mentioned radicals being unsubstituted or monosubstituted or polysubstituted by alkoxy, hydroxyl or halogen, or furthermore are amino, mono- or dialkylamino, phenyl or phenoxy, phenyl and phenoxy independently of one another being unsubstituted or monosubstituted or polysubstituted by halogen or halogenoalkyl, or two adjacent substituents Z together are a divalent group of the formula $-OCH_2O-$, $-S-CH_2-O-$ or $-S-CH_2-S-$, which group is unsubstituted or substituted by alkyl, n is an integer from 0 to 5, X is hydroxyl or alkoxy, alkenyloxy, alkynyloxy, alkylthio or cycloalkoxy, the five last-mentioned radicals being unsubstituted or monosubstituted or polysubstituted by radicals from the group comprising alkoxy, alkylthio, mono- and dialkylamino, phenyl, cyano and halogen, or is furthermore phenoxy, or is furthermore trialkylsilylmethoxy, a radical of the formula

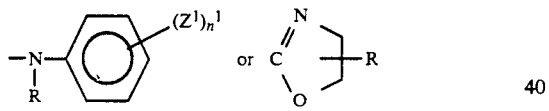

where R in each case is hydrogen or alkyl, $Z^1$ independently of Z has the meanings mentioned above in the case of Z, and $n^1$ is an integer from 0 to 5, or is furthermore amino, mono- or dialkylamino, cycloalkylamino, hydrazino, alkyl- or dialkylhydrazino, pyridino, morpholino, dimethylmorpholino, a radical of the formula

where $R^1$ and $R^2$ independently of one another are alkyl radicals or $R^1$ and $R^2$ together with the carbon atom linking them form a cycloalkyl radical, or is furthermore a radical of the formula

where $R^3$ and $R^4$ independently of one another are hydrogen or alkyl.

11. A method for protecting crop plants against phytotoxic secondary effects of a herbicide, wherein a herbicide is applied to the plants, seeds of the plants or the cropping area in combination with a compound of the formula (I) or a salt thereof

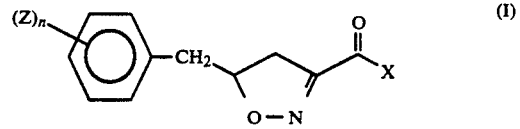

where the radicals independently of one another are halogen, nitro, cyano, or alkyl, alkoxy, alkylthio or cycloalkyl, the four last-mentioned radicals being unsubstituted or monosubstituted or polysubstituted by alkoxy, hydroxyl or halogen, or furthermore are amino, mono- or dialkylamino, phenyl or phenoxy, phenyl and phenoxy independently of one another being unsubstituted or monosubstituted or polysubstituted by halogen or halogenoalkyl, or two adjacent substituents Z together are a divalent group of the formula $-OCH_2O-$, $-S-CH_2-O-$ or $-S-CH_2-S-$, which group is unsubstituted or substituted by alkyl, n is an integer from 0 to 5, X is hydroxyl or alkoxy, alkenyloxy, alkynyloxy, alkylthio or cycloalkoxy, the five last-mentioned radicals being unsubstituted or monosubstituted or polysubstituted by radicals from the group comprising alkoxy, alkylthio, mono- and dialkylamino, phenyl, cyano and halogen, or is furthermore phenoxy, or is furthermore trialkylsilylmethoxy, a radical of the formula

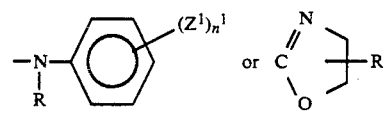

where R in each case is hydrogen or alkyl, $Z^1$ independently of Z has the meanings mentioned above in the case of Z, and $n^1$ is an integer from 0 to 5, or is furthermore amino, mono- or dialkylamino, cycloalkylamino, hydrazino, alkyl- or dialkylhydrazino, pyridino, morpholino, dimethylmorpholino, a radical of the formula

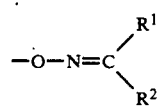

where $R^1$ and $R^2$ independently of one another are alkyl radicals or $R^1$ and $R^2$ together with the carbon atom linking them form a cycloalkyl radical, or is furthermore a radical of the formula

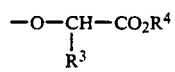

where $R^3$ and $R^4$ independently of one another are hydrogen or alkyl.

* * * * *